(12) United States Patent
Skantze et al.

(10) Patent No.: US 7,780,989 B2
(45) Date of Patent: Aug. 24, 2010

(54) PROCESS FOR THE PREPARATION OF CRYSTALLINE NANO-PARTICLE DISPERSIONS

(75) Inventors: Tommy Urban Skantze, Mölndal (SE); Per Lennart Lindfors, Mölndal (SE); Sara Forssen, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 1096 days.

(21) Appl. No.: 10/521,617

(22) PCT Filed: Jul. 14, 2003

(86) PCT No.: PCT/GB03/03044

§ 371 (c)(1),
(2), (4) Date: Jan. 14, 2005

(87) PCT Pub. No.: WO2004/009057

PCT Pub. Date: Jan. 29, 2004

(65) Prior Publication Data

US 2005/0202092 A1     Sep. 15, 2005

(30) Foreign Application Priority Data

Jul. 18, 2002   (GB) ................ 0216700.5

(51) Int. Cl.
*A61K 9/14*   (2006.01)
(52) U.S. Cl. ..................................... 424/489
(58) Field of Classification Search ............ None
See application file for complete search history.

(56) References Cited

U.S. PATENT DOCUMENTS

| | | | | |
|---|---|---|---|---|
| 4,522,743 A * | 6/1985 | Horn et al. ............... | 516/70 |
| 4,826,689 A | 5/1989 | Violanto et al. | |
| 4,997,454 A | 3/1991 | Violante et al. | |
| 5,118,528 A | 6/1992 | Fessi et al. | |
| 5,145,684 A | 9/1992 | Liversidge et al. | |
| 5,314,506 A | 5/1994 | Midler, Jr. et al. | |
| 5,624,941 A | 4/1997 | Barth et al. | |
| 5,780,062 A | 7/1998 | Frank et al. | |
| 5,843,465 A | 12/1998 | Lundquist | |
| 5,895,659 A * | 4/1999 | Luddecke et al. ....... | 424/442 |
| 5,932,245 A | 8/1999 | Wunderlich et al. | |
| 6,048,550 A | 4/2000 | Chan et al. | |
| 6,074,986 A | 6/2000 | Mulqueen et al. | |
| 6,383,471 B1 | 5/2002 | Chen et al. | |
| 6,432,984 B1 | 8/2002 | Barth et al. | |
| 6,607,784 B2 * | 8/2003 | Kipp et al. ............... | 427/213.3 |
| 6,645,985 B2 | 11/2003 | Barth et al. | |
| 6,884,438 B1 | 4/2005 | Quintanar et al. | |
| 2002/0188007 A1 | 12/2002 | Barth et al. | |
| 2003/0059472 A1 | 3/2003 | Brynjelsen et al. | |
| 2004/0039024 A1 | 2/2004 | Barth et al. | |

FOREIGN PATENT DOCUMENTS

| | | |
|---|---|---|
| CA | 2353809 | 6/2000 |
| EP | 275607 A1 | 7/1988 |
| EP | 0377457 | 7/1990 |
| EP | 0589838 B1 | 8/2001 |
| GB | 2276567 A | 10/1994 |
| JP | 03-188438 | 8/1991 |
| WO | WO-92/18105 | 10/1992 |
| WO | WO-96/24340 | 8/1996 |
| WO | WO 96/32095 | 10/1996 |
| WO | WO-96/35414 | 11/1996 |
| WO | WO-97/04756 | 2/1997 |
| WO | WO-97/11686 | 4/1997 |
| WO | WO-97/13503 | 4/1997 |
| WO | WO 98/14174 A | 4/1998 |
| WO | WO 98/23350 | 6/1998 |
| WO | WO 99/00113 A | 1/1999 |
| WO | WO-99/04766 | 2/1999 |
| WO | WO 99/59709 | 11/1999 |
| WO | WO-00/33820 | 6/2000 |
| WO | WO 00/38811 | 7/2000 |
| WO | WO 00/44468 | 8/2000 |
| WO | WO 0044468 A1 * | 8/2000 |
| WO | WO-00/71079 A2 | 11/2000 |
| WO | WO 01/70700 A1 | 9/2001 |
| WO | WO 01/92293 A2 | 12/2001 |
| WO | WO 02/00199 | 1/2002 |
| WO | WO 02/055059 A2 | 7/2002 |

(Continued)

OTHER PUBLICATIONS

Ruch et al., Journal of Colloid and Interface Science, vol. 229, No. 1, Sep. 1, 2000, p. 207-211.

(Continued)

*Primary Examiner*—S. Tran
(74) *Attorney, Agent, or Firm*—White & Case LLP

(57) ABSTRACT

A process for the preparation of a dispersion of crystalline nanoparticles in an aqueous medium is disclosed. Specifically, a first solution comprising a substantially water-insoluble substance in a water-miscible organic solvent is rapid mixed with an aqueous phase comprising water, and optionally a stabilizer, to form a dispersion of amorphous particles. The dispersion of amorphous particles is then sonicated for a sufficient period to form crystalline nanoparticles of the substantially water-insoluble substance. The process provides nanocrystals with a mean hydrodynamic diameter of less than 1 micron, particularly less than 300 nm, and is particularly useful for the preparation of nanocrystalline dispersions of pharmaceutical substances.

16 Claims, 2 Drawing Sheets

FOREIGN PATENT DOCUMENTS

| | | |
|---|---|---|
| WO | WO 03/035035 | 5/2003 |
| WO | WO 03/051850 A1 | 6/2003 |
| WO | WO 03/051851 A1 | 6/2003 |

OTHER PUBLICATIONS

Sjoestroem B. et al., Journal of Dispersion Science and Technology, vol. 15, No. 1, 1994, p. 89-117.

Sjoestroem B. et al., Journal of Pharmaceutical Sciences, vol. 82, No. 6, Jun. 1, 1993, p. 584-9.

Kasai et al., Jpn. J. Appl. Phys., 1992, 31, L1132.

Kasai et al., Bull. Chem. Soc. Jpn., 1998, 71, 2597.

Mohwald and Talmon, Current Opinion in Colloid and Interface Science, 1997, 2, 129.

E. D. Goddard, Colloids and Surfaces, 1986, 19, 255.

Kabalnov et al., "Ostwald Ripening in Two-Component Disperse Phase Systems: Application to Emulsion Stability", Elsevier Science Publishers B.V., 19-32, 1987.

Steffens et al., "O/W Emulsions as Vehicles for Micronized Drug Particles"; Eur. J. Pharm. Biopharm. 37 (4) 219-226 (1991).

W.I. Higuchi et al., "Physical Degradation of Emulsions Via the Molecular Diffusion Route and the Possible Prevention Thereof"; J. of Pharm. Sciences, vol. 51, No. 5, 459-466, May 1962.

M.J.Harding, "The Influence of Lodide Content on the Ripening Behavior of a Model Emulsion System"; Photographic Science and Engineering, vol. 24, No. 1, 32-44, Jan./Feb. 1980.

K. Lowe, "Second-generation Perfluorocarbon Emulsion Blood Substitutes", Art. Cells, Blood Subs, and Immob Biotech., 28 (1), 25-38, 2000.

Lannibois et al., "Surfactant Limited Aggregation of Hydrophobic Molecules in Water", J. Phys. II France 7, 319-342, 1997.

C. Malcolmson et al., "Effect on Oil on the Level of Solubilization of Testosterone Propionate into Nonionic Oil-in-Water Microemulsions", Journal of Pharmaceutical Sciences, vol. 87, No. 1, 109-116, 1998.

K. Welin-Berger et al., "Inhibition of Ostwald ripening in local anesthetic emulsions by using hydrophobic excipients in the disperse phase", International Journal of Pharmceutics, 200, 249-260, 2000.

Lennart Lindfors et al., "Amorphous Drug Nanosuspensions.1. Inhibition of Ostwald Ripening", Langmuir 2006, 22, 906-910, published on Web Dec. 21, 2005.

Lee, Sang Cheon et al., "Hydrotropic Polymeric Micelles for Enhanced Paclitaxel Solubility: In Vitro and In Vivo Characterization", Biomacromolecules 2007, 8, 202-208.

\* cited by examiner

Cryo-TEM images of crystalline nano-particles of Felodipine.

100 nm

Cryo-TEM images of amorphous nano-particles of Felodipine.

PROCESS FOR THE PREPARATION OF CRYSTALLINE NANO-PARTICLE DISPERSIONS

BACKGROUND OF THE INVENTION

The present invention relates to a process for the preparation of a dispersion of crystalline nano-particles, particularly a dispersion of crystalline nano-particles in an aqueous medium and more particularly to a process for the preparation of a dispersion of crystalline nano-particles comprising a substantially water-insoluble pharmacologically active compound in an aqueous medium.

Dispersions of a solid material in a liquid medium are useful in a number of applications including paints, inks, dispersions of pesticides and other agrochemicals, dispersions of biocides and dispersions of pharmacologically active compounds.

In the pharmaceutical field many pharmacologically active compounds have very low aqueous solubility which can result in low bioavailability when such compounds are administered to a patient. Generally, the bioavailability of such compounds is improved by reducing the particle size of the compound, particularly to a sub-micron size, because this improves dissolution rate and hence absorption of the compound.

The formulation of a pharmacologically active compound as an aqueous suspension, particularly a suspension with a sub-micron particle size, enables the compound to be administered intravenously thereby providing an alternative route of administration which may increase bioavailability compared to oral administration.

Formation of suspensions of crystalline nano-particles (nano-crystals) through direct precipitation is known in the art to be problematic. The rapid precipitation necessary to achieve small particle size often results initially in a suspension of amorphous material. Although the amorphous particles will often crystallise over time, slow crystal growth tends to result in the formation of large crystals with a particle size of >1 micron. Attempts to precipitate crystalline material by direct precipitation is generally difficult to control and results in the formation and growth of large (>1 micron) crystals.

U.S. Pat. No. 4,826,689 describes a process for the preparation of amorphous particles of a solid by infusing an aqueous precipitating liquid into a solution of the solid in an organic liquid under controlled conditions of temperature and infusion rate, thereby controlling the particle size. U.S. Pat. No. 4,997,454 describes a similar process for the preparation of amorphous particles in which the precipitating liquid is non-aqueous. U.S. Pat. No. 5,118,528 also describes a process for preparing a colloidal dispersion of particles using a solvent/anti-solvent precipitation process.

U.S. Pat. No. 5,780,062 describes a process for preparing small stable particles wherein a solution of a substance in an organic solvent is precipitated into an aqueous solution containing polymer/amphiphile complexes.

Generally the amorphous solubility of a substance is significantly higher than the crystalline solubility of the substance. Accordingly, amorphous particles are prone to higher rates of particle growth through solubility driven particle growth mechanisms such as Ostwald ripening compared to crystalline particles. Therefore, crystalline suspensions tend to be stable for significantly longer than dispersions of amorphous particles because the Ostwald ripening occurs at a slower rate in the crystalline particles. Amorphous particle dispersions are also prone to re-crystallise as a more stable crystalline form resulting in the uncontrolled growth of large crystals.

WO98/23350 and WO99/59709 describe processes in which a melt of an organic compound is dispersed in a liquid to form an emulsion. The emulsion is then subjected to ultrasound to give a crystalline dispersion. The particles prepared using the process are of the order 2 to 10 microns.

Crystalline dispersions obtained directly by precipitation are known in the art to be influenced by agitation of the solutions. Various methods of agitation are known in the art (see for example, WO 01/92293), for example mechanical mixing, vibration, micro-wave treatment and sonication.

WO 96/32095 describes a process for the direct formation of crystals by introducing a solution of a substance in a solvent in a droplet form or as a jet into an agitated antisolvent. Agitation is achieved using a number of techniques including ultrasonic agitation. The resulting crystals generally have a mass median diameter of 1 to 6 microns.

U.S. Pat. No. 5,314,506 describes a crystallisation process in which a jet of a solution containing a substance is impinged with a second jet containing an anti-solvent for the substance. The rapid mixing produced by the impinging jets results in a reduction of the crystals so formed compared to conventional slow crystallisation processes. The smallest crystals disclosed are about 3 microns and the majority are in the range of from 3 to 20 microns.

WO 00/44468 describes a modification to the apparatus described in U.S. Pat. No. 5,314,506 wherein ultrasound energy is applied at the point of impingement of the two jets to further enhance localised mixing and is stated to give direct formation of small crystals with a diameter of less than 1 micron. Generally the crystalline particles described have an average size of 0.5 microns.

WO00/38811 describes an apparatus and process wherein crystalline particles suitable for inhalation are prepared by precipitation of a substance from solution using an anti-solvent in a flow-cell mixing chamber in the presence of ultrasonic radiation at the point of mixing the solvent and anti-solvent system. This method results in the direct crystallisation of particles typically having an average particle size of from 4 to 10 microns. WO02/00199 and WO03/035035 describe modifications to the process described in WO00/38811 which reduce crystal agglomeration and enable more efficient isolation of the crystals so formed.

In a novel method of obtaining crystalline nano-particles, Kasai et al (Jpn. J. Appl. Phys., 31, L1132 (1992)) precipitated particles by dropwise addition of an ethanol solution of an organic compound (typically 50 µl with a concentration of 30 mM) into 10 ml of vigorously stirred water giving a total concentration of approximately 0.15 mM. Stirring was then continued for a few minutes and the particle size obtained was about 300 nm. They found that the particle size could be reduced by precipitation at still lower concentrations. By the same procedure Kasai et al (Bull Chem Soc Jpn, 71, 2597 (1998)) formed aqueous suspensions of nano-crystals of perylene at concentrations between 2.5 and 20 µM. However, such low concentrations generally require the sample to be concentrated e.g. by ultrafiltration, before use. Furthermore, if the total initial concentration of organic compounds is increased then the size of particles obtained by such methods is >1 µm. (see e.g. F. Ruch, E. Matijevic, Journal of Colloid and Interface Science, 229, 207 (2000)).

EP 275 607 describes a process wherein ultrasound energy is applied to a suspension of crystals in a liquid phase, the ultrasound being used to fragment the pre-formed crystals. Generally the volume mean diameter of the resulting crystals was 10 to 40 microns.

An alternative approach to direct precipitation is to reduce the particle size of the material prior to suspension, for example by milling as described in U.S. Pat. No. 5,145,684, however this can be disadvantageous as it may be difficult to achieve a sufficiently uniform crystal size. It is particularly important that the particle size in a dispersion of a pharmacologically active compound is as uniform as possible because a difference in particle size is likely to affect the bioavailability and hence the efficacy of the compound. Furthermore, if the dispersion is required for intravenous administration, large particles in the dispersion may render the dispersion unsuitable for this purpose, possibly leading to adverse or dangerous side effects.

There is therefore a need for alternative processes that enable nano-crystals to be formed, particularly nano-crystals of less than 500 nm, more particularly less than 400 nm, especially less than 280 nm and more especially less than 250 nm with a narrow particle size distribution.

BRIEF SUMMARY OF THE INVENTION

We have surprisingly found that dispersions of nano-crystals in an aqueous medium can be prepared using a direct precipitation process, wherein the crystallisation is induced by application of ultrasound.

According to a first aspect of the present invention there is provided a process for the preparation of a dispersion of nano-crystalline particles in an aqueous medium comprising:

combining with rapid mixing:
a) a first solution comprising a substantially water-insoluble substance in a water-miscible organic solvent with;
b) an aqueous phase comprising water and optionally a stabiliser, and thereafter sonicating the resulting mixture for a sufficient period to form nano-crystalline solid particles of the substantially water-insoluble substance; and optionally removing the water-miscible organic solvent.

More particularly there is provided a process for the preparation of a dispersion of nano-crystalline particles in an aqueous medium comprising: combining (preferably under conditions of rapid mixing):
a) a first solution comprising a substantially water-insoluble substance in a water-miscible organic solvent with;
b) an aqueous phase comprising water and optionally a stabiliser, to form a dispersion of amorphous particles; and
c) sonicating the dispersion of amorphous particles for a sufficient period to form nano-crystalline particles of the substantially water-insoluble substance; and optionally removing the water-miscible organic solvent.

In this specification, by crystalline nano-particles or nano-crystals or nano-crystalline particles, we mean crystalline particles with a particle size of less than one micron.

The crystals in the dispersion preferably have a mean particle size of less than 1 μm and more preferably less than 500 nm. It is especially preferred that the crystals in the dispersion have a mean particle size of from 10 to 500 nm, more particularly from 10 to 280, more particularly from 30 to 280 nm, especially from 50 to 250 nm and still more especially from 100 to 200 nm. By the term "mean particle size" used herein is meant the mean hydrodynamic diameter of a particle (for example the crystalline or amorphous particles present in the dispersion) as measured using conventional techniques, for example by dynamic light scattering using a BeckmanCoulter N4 plus apparatus. Dynamic light scattering allows the diffusion coefficient D, to be determined, from which the hydrodynamic diameter can be calculated using the Stoke-Einstein equation: $D=kT/(3\pi\eta d_H)$, where k is the Boltzmann constant, T temperature, $\eta$ the viscosity of the solvent and $d_H$ hydrodynamic diameter (for example as described in "Introduction to Colloid and Surface Chemistry", D. J. Shaw, Butterworths, 1980). The crystals may also suitably be examined and their size and shape determined using cryo Transmission Electron Microscopy, for example a Zeiss EM 902 (see for example H. Mohwald, Y. Talmon, Current Opinion in Colloid and Interface Science, 2, 129 (1997)). Suitable microscopy conditions are described herein under the Examples section.

The nano-crystalline particles prepared according to the present invention exhibit a narrow particle size distribution, by which is meant that in general that 99% (on a volume base) of the particles lie within ±150 nm of the mean hydrodynamic diameter. The particle size distribution may be calculated by deconvolution using for example the CONTIN algorithm and an assumed particle refractive index of 1.59.

The nano-crystalline particles prepared according to the present process are substantially free from non-crystalline material, by which is meant that the nano-crystalline particles are at least 70, 80, 85, 90, 95, 99% and particularly 100% crystalline. The degree of crystallinity can be determined using suitable known techniques, for example X-ray crystallography and/or differential scanning calorimetry (DSC) analysis and/or Raman spectroscopy.

The substantially water-insoluble substance in the first solution is preferably a substantially water-insoluble organic substance. By substantially insoluble is meant a substance that has a solubility in water at 25° C. of less than 0.5 mg/ml, preferably less than 0.1 mg/ml and especially less than 0.05 mg/ml The solubility of the substance in water may be measured using a conventional technique. For example, a saturated solution of the substance is prepared by adding an excess amount of the substance to water at 25° C. and allowing the solution to equilibrate for 48 hours. Excess solids are removed by centrifugation or filtration and the concentration of the substance in water is determined by a suitable analytical technique such as HPLC.

The process according to the present invention may be used to prepare aqueous dispersions of nano-crystalline particles of a wide range of substantially water-insoluble substances. Suitable substances are those which are known to be able to crystallise in at least one solvent-non-solvent system. Suitable substances include but are not limited to pigments, pesticides, herbicides, fungicides, industrial biocides, cosmetics and pharmacologically active compounds.

A further aspect of the invention comprises nano-crystalline particles of a substance made by the process of the current invention.

In a preferred embodiment the substantially water-insoluble substance is a substantially water-insoluble pharmacologically active compound. Numerous classes of pharmacologically active compounds are suitable for use in the present invention including but not limited to, substantially water-insoluble anti-cancer agents, steroids, preferably glucocorticosteroids (especially anti-inflammatory glucocorticosteroids, for example budesonide) antihypertensive agents (for example felodipine or prazosin), beta-blockers (for example pindolol or propranolol), ACE inhibitors, angiotensin II receptor antagonists. hypolipidaemic agents, aniticoagulants, antithrombotics, antifungal agents (for example griseofulvin), antiviral agents, antibiotics, antibacterial agents (for example ciprofloxacin), antipsychotic agents, antidepressants, sedatives, anaesthetics, anti-inflammatory agents (for example ketoprofen), antihistamines, hormones (for example testosterone), immunomodifiers, or contraceptive agents. Particular examples of substantially water-insoluble pharmacologically active compound include anticancer agents such as bicalutamide, angiotensin II receptor antagonists such as candersartan cilexitil, antihypertensive agents such as felodipine and $CB_1$ modulators (known as antagonists or inverse agonists) useful in the treatment of obesity, psychiatric and neurological disorders for example those disclosed in EP 656354, WO00/46209, WO01/70700, PCT application numbers PCT/GB02/05736 and PCT/GB02/05742.

DETAILED DESCRIPTION OF THE INVENTION

Water-Miscible Organic Solvent

Figure 1A:
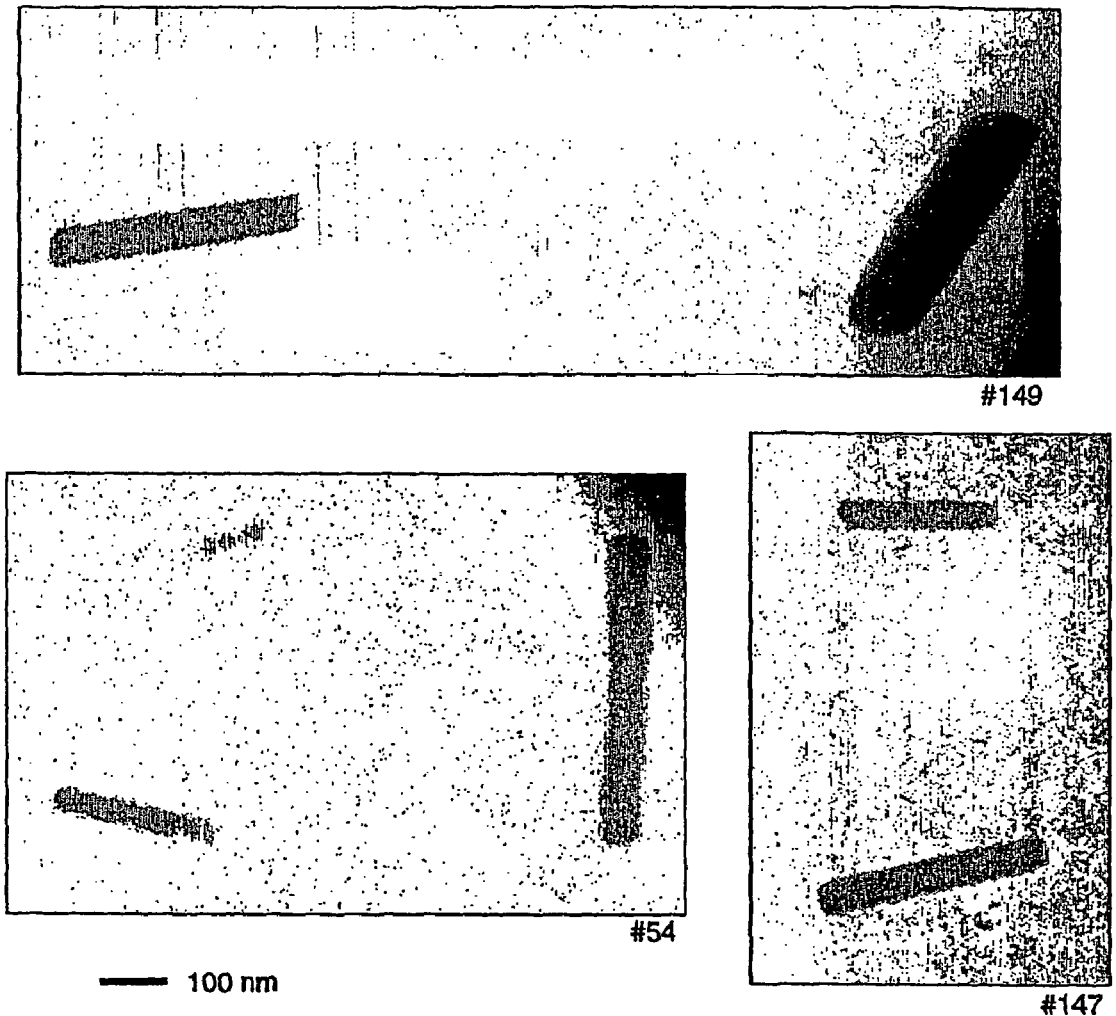
FIG. 1a shows cryo-TEM images of Felodipine nano-crystals prepared using the process according to the present invention.

The water-miscible organic solvent in the first phase is preferably miscible with water in all proportions. The water-miscible organic solvent should also be a solvent for the substantially water-insoluble substance. The water-miscible organic solvent is selected such that the substantially water-insoluble substance has a sufficient solubility in the water miscible organic solvent to enable a precipitate of the substantially water-insoluble substance to form when the first solution is combined with the aqueous phase. Suitably, the substantially water-insoluble substance has a solubility of 10 mg/l or more in the water-miscible organic solvent.

Generally it is preferred that the concentration of the substantially water-insoluble substance in the water-miscible organic solvent is as high as possible to aid efficient precipitation and reduce the quantity of organic solvent required. The upper concentration of the substantially water-insoluble substance in the water-miscible organic solvent is determined by the solubility of the substance in the solvent. However, we have found that a wide range of concentrations may be used in the present process. Typically, a concentration of substantially water-insoluble substance of 1% by weight or more in the organic solvent is suitable.

The substantially water-insoluble substance should be fully dissolved in the water-miscible organic solvent. The presence of particles of the substantially water-insoluble substance may result in poor control of the particle size distribution in the dispersion.

If required the solubility of the substantially water-insoluble substance in the water-miscible organic solvent can be increased by heating a mixture of the substantially water-insoluble substance and water-miscible organic solvent to provide a solution. The solution is then maintained at elevated temperature until it is combined with the aqueous phase in the process.

As will be understood, the selection of water-miscible organic solvent will be dependent upon the nature of the substantially water-insoluble substance. When the substantially water-insoluble substance is an organic compound the water-miscible organic solvent should have a sufficiently low dielectric constant to be able to dissolve the substantially water-insoluble substance. Suitable water-miscible solvents for dissolving a substantially water-insoluble organic substance include, a water-miscible alcohol, for example methanol ethanol n-propyl alcohol isopropyl alcohol, tert-butyl alcohol, ethylene glycol or propylene glycol; dimethylsulfoxide; dimethylformamide; N-methylpyrrolidone; a water-miscible ether, for example tetrahydrofuran; a water-miscible nitrile, for example acetonitrile; a water-miscible ketone, for example acetone or methyl ethyl ketone; dimethylacetamide or a mixture of two or more of the above mentioned water-miscible organic solvents.

Precipitation

In the present process the first solution and the aqueous phase may be combined by, for example, adding the first solution to the aqueous phase, or by adding the aqueous phase to the first solution, or by combining the first solution and the aqueous phase substantially simultaneously under conditions which promote the formation of a dispersion of amorphous particles. Conveniently the first solution and the aqueous phase may be combined by adding the first solution to the aqueous phase with rapid mixing.

Preferably the first solution, and aqueous phase are mixed rapidly during the combination to promote a high degree of turbulence and the formation of a uniform dispersion of amorphous particles.

In one embodiment of the present invention rapid mixing of the first solution and the aqueous phase is conveniently achieved by sonication during the combination. Alternatively other agitation methods known in the art may be used, provided that the rate of agitation is sufficiently high to result in amorphous particles, preferably with a<1 μm particle size. Examples of suitable methods which may be used for rapidly mixing the first solution and aqueous phase include rapid agitation during mixing using conventional stirring to promote turbulence during the combination. Alternatively the first solution and aqueous phase may be combined by jet mixing, for example using the apparatus described in U.S. Pat. No. 5,314,506 or WO 00/44468, provided that the precipitation conditions are controlled to give an initial dispersion of amorphous particles. The precipitation may also be performed using a batch process wherein a batch of the first liquid is combined with a fixed volume of the aqueous phase in a suitable mixing vessel. Alternatively, the combination may be operated on a continuous or semi-continuous basis using, for example a flow cell to as a means for mixing a flowing stream of the first solution with a flowing stream of the aqueous phase. The resultant dispersion of amorphous particles may then be collected in a down-stream vessel(s) for subsequent sonication and conversion to the suspension of nano-crystalline particles.

As discussed herein, the precipitation conditions should be controlled to provide an amorphous dispersion of particles upon combination of the first solution and the aqueous phase. By "amorphous dispersion of particles" is meant a dispersion of amorphous particles in a liquid medium which is substantially free from crystalline particles when the first solution and aqueous phase are combined. The Inventors have found that the presence of even small amounts of crystalline material in the amorphous dispersion prior to sonication promotes the formation of large crystals during the subsequent sonication, thereby preventing formation of the desired uniform dispersion of nano-crystalline particles. Suitably the suspension of amorphous particles should contain less than 0.01% by weight, particularly less than 0.001% and more particularly less than 0.0001% by weight of crystalline particles to avoid the undesirable formation of large crystals during the subsequent steps of the process. For example the initial dispersion of amorphous particles could contain 0.00001 to 0.0001% by weight crystalline material, although as mentioned above it is preferred that no detectable crystalline material is present. The required "purity" (i.e. non-crystallinity) of the initial amorphous dispersion will be evidenced by the subsequent sonication stage in the process. If crystalline material is present sonication will result in the undesirable growth of large particles (>1 micron) rather than the required nano-crystalline particles.

The precipitation conditions required for the formation of an amorphous dispersion of particles will depend to some extent upon, for example, the particular material, the solvent used, the particular precipitation apparatus used and the method for agitating/combining the first solution and the aqueous phase. The rapid precipitation conditions used in the present process favors the formation of kinetically stable amorphous particles. The required conditions may be determined using routine experimentation to optimise the precipitation conditions for the formation of amorphous particles.

The Inventors have found that when the first solution is added to the aqueous phase or vice versa that the final concentration of the substantially water-insoluble substance in the combined solution is influential in the formation of an amorphous dispersion. Generally, a concentration of substantially water-insoluble substance about 10 mM or less, in the combined solution and aqueous phase will minimise the formation of crystalline material (as will be understood, the molar concentrations used herein refers to a molar concentration per liter). Higher concentrations of substantially water-insoluble substance can result in the formation of crystalline material in the dispersion formed during the precipitation.

Accordingly in an embodiment of the present invention the concentration of substantially water-insoluble substance is from 0.2 to 10 mM, particularly from 0.5 to 5 mM and more particularly from 0.5 to 3 mM, especially about 1 mM, wherein the concentration refers to the molar concentration of substantially water-insoluble substance of combined first solution and aqueous phase (and where concentration here refers to the total amount of substance present in the combined liquids, including the suspended amorphous particles and any of the substance that may be dissolved in the combined liquid medium).

In a preferred embodiment the first solution and the aqueous phase are combined rapidly. The Inventors have found that rapid combination promotes the formation of small (generally of a nano-particle size) amorphous particles. Therefore, in embodiments where, for example, the first solution is added to an agitated aqueous phase it is preferred that the first solution is added to the aqueous phase as a single charge of material, rather than as a slow infusion into the aqueous phase. On the small scale this may be achieved by simply pouring all of the first solution directly into the agitated aqueous phase. On a larger scale rapid addition may be achieved by pumping the first solution into the aqueous phase at a high mass transfer rate. Preferably the combination of the first solution and aqueous phase takes place in less than 1 minute, more preferably less than 30 seconds and particularly less than 10 seconds, more particularly less than 5 seconds, for example from 1 to 10 seconds) such that the combination is substantially instantaneous.

The particle size of the amorphous particles formed by the initial precipitation need not be less than 1 micron. However, it is preferred that the particle size of the amorphous particles is similar to that of the required crystalline nano-particles. Accordingly it is preferred that the combination of the first solution and the aqueous phase produces a uniform dispersion of amorphous particles with a mean particle size of less than 1 μm and more preferably less than 500 nm. It is especially preferred that the amorphous particles have a mean particle size of from 10 to 500 nm, particularly from 10 to 280 nm, more particularly from 30 to 280 nm, more especially from 50 to 250 nm and still more especially from 100 to 200 nm.

Temperature during the precipitation is not considered to be critical and may conveniently be carried out at about ambient temperature (for example 15 to 25° C.), although higher or lower temperatures may be used if required. However, in embodiments of the invention it may be advantageous to cool the aqueous phase to increase the ratio between the amorphous and crystalline solubility, thus, increasing the supersaturation and the nucleation rate to obtain smaller particles as discussed below in relation to sonication.

Accordingly, in a particular embodiment of the invention, the first liquid is combined with the aqueous phase under conditions of high turbulence (for example by rapid stirring, sonication or by a combination of rapid stirring and sonication), wherein the combination takes place rapidly (preferably in less than 30 seconds, more preferably less than 10 seconds for example from 1 to 10 seconds), and wherein the final concentration of the substantially water-insoluble substance in the combined first solution and aqueous phase is 10 mM or less (preferably less than 5 mM and particularly a final concentration of about 1 mM). The Inventors have found that these conditions promote the formation of a uniform dispersion of amorphous particles with a mean particle size of less than 1 micron.

Some particles will precipitate and form a uniform dispersion of amorphous particles without the need for a stabiliser in the aqueous phase. However, we have found that amorphous particles often aggregate upon precipitation or during the subsequent sonication unless a stabiliser is present in the aqueous phase.

Stabilisers suitable for the prevention of particle aggregation in dispersions are well known to those skilled in the art. Suitable stabilisers include dispersants and surfactants which may be anionic, cationic or non-ionic. Suitable dispersants include, a polymeric dispersant, for example a polyvinylpyrrolidone, a polyvinylalcohol or a cellulose derivative, particularly a water-soluble or water-dispersible cellulose derivative, for example hydroxypropylmethyl cellulose, hydroxyethyl cellulose, ethylhydroxyethyl cellulose or carboxymethyl cellulose. A preferred polymeric dispersant is polyvinylpyrrolidone (PVP). A wide range of PVP polymers may be used, for example a PVP with a molecular weight in the range of from 10,000 to 100,000 Daltons, such as 50,000 to 60,000. Suitable anionic surfactants include alkyl or aryl sulfates example, sodium dodecyl sulfate. Other suitable ionic surfactants include for example alkyl and aryl carboxylates for example, sodium or potassium myristate or sodium laurate; di-alkyl sulfosuccinates, particularly di-(4-12C)alkyl sulfosuccinates, such as sodium, calcium or potassium dioctyl sulfosuccinate (e.g. Docusate sodium or Aerosol OT) or sodium diamyl sulfosuccinate (Aerosol AY); or bile acid salts, such as salts of deoxycholic acid, taurocholic acid, or glycocholic acid, for example a sodium salt of a bile acid such as sodium taurocholate, sodium deoxycholate or sodium glycocholate; Suitable cationic surfactants include quaternary ammonium compounds and fatty amines. Particular cationic surfactants include alkylammonium compounds (for example (8-22C) alkylammonium, particularly (8-20C)alkylammonium compounds, such as halides) including, for example, laurylammonium chloride; alkyltrimethyl ammonium compounds (for example (8-22C) alkyltrimethyl ammonium, particularly (8-20C)alkyltrimethyl ammonium compounds, such as halides) for example cetyltrimethylammonium bromide (Cetramide), trimethyltetradecylammonium bromide (Myristamide) or lauryl trimethylammonium bromide (Lauramide); benzalkonium halides (such as (8-20C)alkylbenzyldimethylammonium halides, particularly (8-18C)alkylbenzyldimethylammonium halides and mixtures thereof), for example benzalkonium chloride; or alkylpyridinium compounds such as (8-20C)alkylpyridinium compounds, for example cetylpyridinium chloride or bromide.

Suitable non-ionic surfactants include, monoesters of sorbitan which may or may not contain polyoxyethylene residues (for example Tween surfactants such as Tween 20, Tween 40, Tween 60 and Tween 80), ethers formed between fatty alcohols and polyoxyethylene glycols, polyoxyethylene-polypropylene glycols, an ethoxylated castor oil (for example Cremophor EL), ethoxylated hydrogenated castor oil, ethoxylated 12OH-stearic acid (for example Solutol HS15). Further suitable non-ionic surfactants include, for example ethylene oxide-propylene oxide co-polymers, particularly block co-polymers (poloxomers) such as Pluronic, Tetronic or Lutrol surfactants such as Lutrol F68 or Lutrol F127; or polyethoxylated sorbitan fatty acid ester such as Polysorbate 80. Other suitable surfactants are well known to those skilled in the art and can be selected accordingly. Additional surfactants that may be suitable for use in the present invention include, for example, the surfactants listed in U.S. Pat. No. 6,383,471, Table 1.

The aqueous phase may contain a single stabiliser or a mixture of two or more stabilisers. In a preferred embodiment the aqueous phase contains a polymeric dispersant and an amphiphilic surfactant, which may be non-ionic, anionic or cationic. In particular a combination of a polymeric dispersant and an anionic surfactant, for example a polyvinylpyrrolidone and sodium dodecyl sulfate.

When the substantially water-insoluble material is a pharmacologically active compound it is preferred that the stabiliser is a pharmaceutically acceptable material.

In an alternative embodiment the stabiliser may be added to the first solution prior to combination with the aqueous phase. Suitable stabilisers are as hereinbefore described.

Optionally, additional stabiliser may be added to the dispersion after precipitation of the amorphous particles into the aqueous phase to provide additional inhibition of particle aggregation in the dispersion. Stabiliser(s) may also be added to the final dispersion of nano-crystalline particles following the sonication if required, for example to inhibit agglomeration of the nano-crystals.

Generally it is desirable to minimise the quantity of stabiliser present, particularly when the substantially water-insoluble material is a pharmacologically active compound to minimise possible side effects associated with the stabiliser and/or to minimise interactions with the pharmacologically active compound which may be detrimental to the efficacy of the compound. Accordingly, it is generally preferred that the quantity of stabiliser should be the minimum that is required to stabilise amorphous particles and/or final dispersion of nano-crystalline particles. Generally the aqueous phase will contain from 0.001 to 2% by weight, particularly 0.01 to 1% by weight, preferably from 0.05 to 0.5% by weight and especially from 0.1 to 0.2% by weight of stabiliser. When a surfactant is used it is preferred that the surfactant is present at a concentration below the critical micelle concentration to avoid solubilisation of the nano-crystals into the liquid medium.

In one embodiment of the invention the aqueous phase contains a polymeric dispersant and an amphiphilic surfactant, for example a polyvinylpyrrolidone and sodium dodecyl sulfate. The amphiphilic surfactant is present at a concentration which is above the critical association concentration with the polymeric dispersant, but at a concentration below the critical micelle concentration. This enables polymer-amphiphile aggregates to form as described in U.S. Pat. No. 5,780,062. Accordingly, in this embodiment the process described in U.S. Pat. No. 5,780,062 may be used, provided the precipitation conditions are controlled to give an initial dispersion of amorphous particles as required by the present invention. The critical association concentration of surfactant in a polymer-surfactant system may be determined using known methods (for example as described in E. D. Goddard, *Colloids and Surfaces,* 19, 255 (1986)). For example when the surfactant is sodium dodecylsulfate (SDS) and the polymer is PVP the critical association concentration of SDS is 3 mM. Accordingly in this embodiment the SDS concentration should be between the critical association concentration (about 3 mM) and the critical micelle concentration (about 8 mM).

In a preferred embodiment of the invention the aqueous phase contains a polymeric dispersant and an amphiphilic surfactant, for example a polyvinylpyrrolidone and sodium dodecyl sulfate. In this embodiment surfactant is present at a concentration which is below the critical association concentration with the polymeric dispersant and an anionic surfactant. Thus in the case when the aqueous phase contains a polyvinylpyrrolidone and sodium dodecyl sulfate the concentration of SDS is below 3 mM, for example 0.1 to 2.8 mM, particularly about 0.25 mM. We have found that this embodiment provides a particularly stable dispersion of amorphous particles, whilst using only a small amount of stabiliser.

As mentioned above, the combination of the first solution and aqueous phase in the process according to the present invention results in very fast, substantially instantaneous precipitation of particles of the substantially water-insoluble material to give particles of the desired size with a narrow particle size distribution. Prolonged sonication of this suspension results in formation of nano-crystals of the desired size with a similarly narrow particle size distribution.

Without wishing to be bound by theory, it is thought that the formation of the initial suspension of amorphous particles following combination of the first solution with the aqueous phase promotes the subsequent formation of a uniform dispersion of nano-crystalline particles during the subsequent sonication. Generally the amorphous solubility of a material is higher than the crystalline solubility, for example in the case of felodipine the crystalline solubility is 2 µM compared to an amorphous solubility of approximately 24 µM. It is thought that the presence of the dispersion of amorphous particles during the sonication provides a reservoir of material in solution for the crystallisation step and thereby maintains a high and constant level of super-saturation relative to the crystalline solubility because of the higher amorphous solubility. The high and relatively constant degree of super-saturation provided by the presence of the amorphous particles provides favorable conditions for the formation of a large number of primary nuclei upon application of the ultrasound to the dispersion of amorphous particles. It thought that the maintenance of the high level and relatively constant state of super-saturation during sonication promotes continued primary nucleation and therefore favors the growth of large numbers of small crystalline nano-particles. The high degree of nucleation induced by the sonication and during the crystallisation is thought to promote the formation of crystalline particles with a uniform particle size as a result of the relatively constant level of super-saturation. During the sonication process it is thought that the amorphous material is gradually consumed as it dissolves into the liquid medium and is re-precipitated as the crystalline nano-particles.

In conventional precipitation processes which give crystalline dispersions directly, the initial formation of crystalline particles generally results in a reduction in the degree of super-saturation and promotes the rapid growth of the initial crystals formed, thereby favoring the formation of larger (generally micron sized) crystals. Similarly, if the initial dispersion of amorphous particles also contains crystalline material the crystals present will generally result in the rapid growth of large crystals during sonication rather than the required crystalline nano-particles according to the present invention.

Sonication

By sonication, we mean application of ultrasound to the mixture resulting from the combination of the first solution and the aqueous phase.

According to the process of the present invention, combination of the first solution and the aqueous phase with rapid mixing results in an initial precipitate of amorphous particles of the substantially water-insoluble compound, wherein (in preferred embodiments) the amorphous particles have a particle size<1 μm.

After combination is complete, the mixture is sonicated until crystallisation of the amorphous precipitate occurs. A sufficient period for sonicating the mixture after combination is therefore a period sufficient for substantially complete conversion of amorphous particles into crystalline particles (for example for conversion of 70, 80, 90, 95 or 95% of the amorphous particles to crystalline nano-particles). A suitable sufficient period is for example at least 10 minutes, particularly at least 20 minutes, such as from 10-200 minutes, preferably 20 to 200 minutes, more preferably 10-120 minutes and especially 20-100 minutes. It will be appreciated that the time required may depend upon a number of factors, for example the nature of the sparingly-water soluble compound, the ultrasound frequency, the volume of the solutions used and energy output of the sonication equipment.

The ultrasound frequency should be selected to promote crystallisation of the suspension of amorphous particles. Generally a frequency about 16 kHz or more is suitable, for example in the range of 20 to 100 kHz, more particularly from 20 to 50 kHz. The power required will depend upon the volume of the suspension to which the ultrasound is applied. Generally a power of about 5 W or higher is suitable, for example from 5 to 5000 W, particularly from 200 to 4000 W. The intensity of the ultrasound energy may be adjusted between wide limits.

The ultrasound may be applied using well-known methods. For example the ultrasound may be applied directly by means of, for example an ultrasonic probe or horn placed in the liquid medium. Alternatively the ultrasound may be applied by means of an ultrasonic bath or coupled to the vessel containing the amorphous particles by means of a coupling device such as transmission from an ultrasound transducer into the suspension via a fluid-filled probe into the vessel containing the suspension.

Suitable sonication equipment is well known to those skilled in the art and can be selected accordingly. Conveniently on a laboratory scale, sonication equipment with an ultrasonication frequency of 35 kHz and a power output of 285 W may be used, for example an Elma Transsonic Bath T460/H. On a non-laboratory scale a sonoreactor, for example from AEA Technology could be used, such as that described in GB 2,276,567.

The temperature during sonication is not considered to be critical and generally a temperature below 50° C. will be suitable. However, we have found that low temperatures generally favor the formation of smaller crystalline particles. Accordingly in an embodiment of the present invention the temperature during sonication of the amorphous dispersion is less than 50° C., particularly less than 45° C. for example from 0 to 45° C., preferably from 1 to 35° C. and especially 5 to 10° C. Without wishing to be bound by theory it is thought that lower temperatures result in a higher level of super-saturation during sonication and increases the degree of primary nucleation during sonication thereby giving a higher number of smaller crystalline particles.

Optionally the water-miscible organic solvent can be removed from the dispersion after the crystallisation. Suitable methods for removing the water-miscible organic solvent are well known and include evaporation, for example by heating the dispersion under vacuum, reverse osmosis, dialysis, ultra-filtration or cross-flow filtration.

If desired the dispersion may be concentrated after crystallisation by removing excess water from the dispersion, for example by evaporation.

Optionally additional components may be added to the liquid media used in the present invention to modify the properties as required, for example to the first solution, the aqueous phase, the dispersion of amorphous particles or to the dispersion of nano-crystalline particles. Examples of such components include viscosity modifying agents, buffers, taste masking agents, anti-oxidants, preservatives, additives to adjust pH or colorants. The additional components may be added before, or more preferably, after the precipitation of the particles.

According to a further embodiment of the present invention there is provided a process for the preparation of a dispersion of nano-crystalline particles of a substantially water-insoluble pharmacologically active substance in an aqueous medium comprising:

combining with rapid mixing:
(a) a first solution comprising the substantially water-insoluble pharmacologically active substance in a water-miscible organic solvent with;
(b) an aqueous phase comprising water and optionally a stabiliser, and thereafter sonicating the resulting mixture for a sufficient period to form nano-crystalline solid particles of the substantially water-insoluble pharmacologically active substance; and optionally removing the water-miscible organic solvent.

In particular this embodiment provides a process for the preparation of a dispersion of nano-crystalline particles of a substantially water-insoluble pharmacologically active substance in an aqueous medium comprising:

combining (preferably with rapid mixing):
(a) a first solution comprising the substantially water-insoluble pharmacologically active substance in a water-miscible organic solvent with
(b) an aqueous phase comprising water and optionally a stabiliser, to form a dispersion of amorphous particles; and
(c) sonicating the dispersion of amorphous particles for a sufficient period to form nano-crystalline particles of the substantially water-insoluble pharmacologically active substance; and optionally removing the water-miscible organic solvent.

This embodiment of the present invention provides dispersions of nano-crystalline crystals of a solid substantially water-insoluble pharmacologically active substance in an aqueous medium. Suitable process conditions for this embodiment are as hereinbefore described.

If required the nano-crystalline particles present in the dispersion prepared according to the present invention may be isolated from the aqueous medium following crystallization (or removal of the water-miscible organic solvent). The nano-crystalline particles may be separated using conventional techniques, for example by centrifuging, reverse osmosis, membrane filtration, lyophilisation or spray-drying. Isolation of the nano-crystalline particles is useful when the particles comprise a substantially water-insoluble pharmacologically active compound because it allows the crystals to be washed and re-suspended in a sterile aqueous medium to give a suspension suitable for administration to a warm blooded mammal (especially a human), for example by oral or parenteral (e.g. intravenous) administration. It may be preferable not to isolate the crystals but instead use the dispersion as formed, for example because isolation of crystals of a particular substance results in the formation of tightly bound aggregates.

In another embodiment of the present invention the process is performed under sterile conditions, thereby providing a sterile dispersion directly which can be administered to a warm blooded mammal as described above without the need for additional purification or sterilisation steps. Alternatively, the dispersion may be sterile filtered following crystallisation and optional removal of the water-miscible organic solvent to leave a sterile suspension.

According to a further aspect of the present invention there is provided an aqueous dispersion comprising a continuous aqueous phase in which is dispersed nano-crystalline particles of a substantially water-insoluble substance obtainable by the process according to the present invention.

Preferably the substantially water-insoluble substance is a substantially water-insoluble pharmacologically active material as described above.

Preferably the concentration of nano-crystalline particles in the dispersion is greater than 0.25 mM, for example from 0.25 to 10 mM, particularly from 0.5 to 5 mM. The nano-crystalline particle(s) of a substantially water-insoluble substance have a particle size as hereinbefore defined.

According to a further aspect of the present invention there is provided nano-crystalline particle(s) of a substantially water-insoluble substance obtainable by the process according to the present invention. Preferably the substantially water-insoluble substance is a substantially water-insoluble pharmacologically active material as described above. The nano-crystalline particle(s) of a substantially water-insoluble substance have a particle size as hereinbefore defined.

According to a further aspect of the present invention there is provided a pharmaceutical composition comprising nano-crystalline particle(s) of a substantially water-insoluble pharmacologically active material in association with a pharmaceutically acceptable diluent or carrier.

When the substance is a substantially water-insoluble pharmacologically active material, the dispersions according to the present invention may be administered to a warm blooded mammal (especially a human), for example by oral or parenteral (e.g. intravenous) administration. In an alternative embodiment the dispersion may be used as a granulation liquid in a wet granulation process to prepare granules comprising the substantially water-insoluble pharmacologically active material and one or more excipients. The resulting granules may then be used directly, for example by filling into capsules to provide a unit dosage containing the granules. Alternatively the granules may be optionally mixed with further excipients, disintegrants, binders, lubricants etc. and compressed into a tablet suitable for oral administration. If required the tablet may be coated to provide control over the release properties of the tablet or to protect it against degradation, for example through exposure to light. Wet granulation techniques and excipients suitable for use in tablet formulations are well known in the art.

The nano-crystalline particles of a pharmacologically active material prepared using the present process may also be used in other pharmaceutical formulations, including but not limited to dry blended compositions such as capsule and direct compression tablet formulations; and controlled or sustained release formulation wherein the particles are dispersed within a suitable matrix, for example in a water-swellable or water-erodible matrix or a biodegradable polymeric matrix.

According to a further aspect of the present invention there is provided nano-crystalline particle(s) of a substantially water-insoluble substance obtainable by the process according to the present invention for use as a medicament.

The process according to the present invention may be useful for promoting the crystallisation of certain materials which are difficult to crystallise using conventional crystallisation methods. It is well known that some substances are very difficult to crystallise from solution and often much trial end error is required to obtain a process that will provide a material in crystalline form. The unique conditions of constant super-saturation provided by the presence of the amorphous dispersion in the present invention may provide nano-crystals of a material that could not be crystallised using known conventional crystallisation methods. The resulting nano-crystals prepared using the present invention can then be used as seed crystals to promote crystallisation in more conventional crystallisation processes. For example, the preparation of a crystalline pharmaceutical compound is often advantageous, because it may enables the compound to be prepared in a highly pure form. A crystalline form may also offer other advantages such as stability and material handling advantages.

According to a further aspect of the present invention there is provided the use of a nano-crystalline particle(s) of a substantially water-insoluble substance obtainable by the process according to the present invention as seed crystals in a crystallisation process. Suitable crystallization processes in which the seed crystals may be used are well known in the art and include, for example systems which induce super-saturation by slow cooling, evaporation or the addition of an anti-solvent.

Process

In the following Examples, sonication was carried out using an Elma Transsonic Bath T460/H with a volume of 2.75 liter, a power consumption of 285 W and an ultrasonication frequency of 35 kHz.

Images shown in the Examples section and analysis of the crystalline or amorphous state of the particles were taken with cryo-TEM (cryo Transmission Electron Microscopy) using undiluted nano-particle suspensions at 25° C. in CEVS (Controlled Environment Vitrification system). The samples were applied as a thin film on a metal plate coated with a porous polymer film, vitrified in liquid ethane at −170° C. and studied at the boiling temperature of nitrogen in a Zeiss EM 902 (accelerator voltage 80 kV).

The mean particle hydrodynamic diameters referred are intensity-weighted numbers obtained from dynamic light scattering measurements using an N4 Plus Beckman Coulter and the Brookhaven Fiber-Optic Quasi-Elastic Light Scattering (FOQELS) instrument.

EXAMPLES

The present invention will be illustrated but not limited by the following examples.

In the examples the polyvinylpyrrolidone used was PVP K30 (ex. BASF) which has a weight-average molecular weight of 57000. In all the examples sodium dodecylsulfate was used together with the PVP as a stabiliser. The SDS concentration used was 0.25 mM in the aqueous phase.

Example 1

Felodipine

A solution of 100 mM Felodipine in dimethylacetamide was prepared. 0.010 ml of this solution was added rapidly to 0.990 ml of an aqueous solution containing 0.2% w/w polyvinylpyrrolidone and 0.25 mM sodium dodecyl sulfate under sonication. The sonication was continued for 30 minutes. The resulting particles were crystalline with a mean hydrodynamic diameter of 165 nm (no change in particle size was observed over 2 hours). Cryo-TEM images of the particles are shown in FIG. 1a.

Comparative Example 1

Figure 1B:
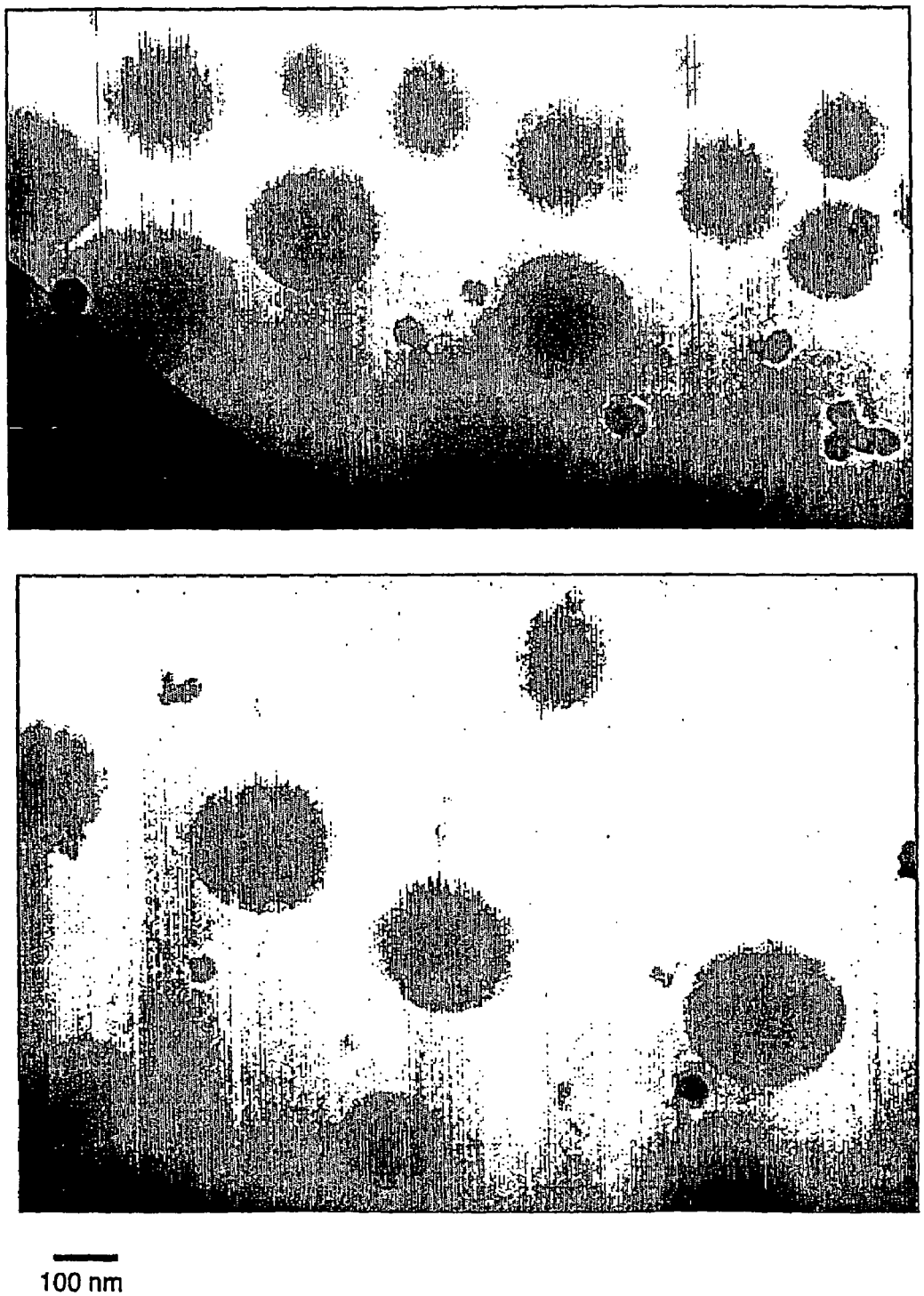
FIG. 1b shows cryo-TEM images of Felodipine amorphous particles prepared according to Comparative Example 1.

The process of Example 1 was repeated but sonication was discontinued directly after mixing the two solutions. The process produced amorphous particles with a mean particle hydrodynamic diameter of approximately 170 nm. The particle size increased due to Ostwald ripening over a period of 1 hour from 170 to 250 nm, and after 2 hours the size was 370 nm. A cryo-TEM image of the particles taken approximately 20 minutes after mixing are shown in FIG. 1b.

Example 2

Candesartan cilexitil

A solution of 100 nM Candesartan cilexitil in dimethylacetamide was prepared. 0.010ml of this solution was added rapidly to 0.990 ml of an aqueous solution containing 0.2% w/w polyvinylpyrrolidone and 0.25 mM sodium dodecyl sulfate under sonication. The sonication was continued for 75 minutes. The resulting particles were crystalline with a mean hydrodynamic diameter of 170 nm.

Comparative Example 2

Example 2 was repeated except sonication was discontinued directly after mixing the two solutions. Amorphous particles were obtained with a mean hydrodynamic diameter of 70 nm.

Example 3

N'-[(1E)-(1-benzyl-1H-indol-3-yl)methylene]benzohydrazide

A solution of 100 mM N'-[(1E)-(1-benzyl-1H-indol-3-yl)methylene]benzohydrazide (commercially available from Interchim, France) in dimethylacetamide was prepared. 0.010 ml of this solution was added rapidly to 0.990 ml of an aqueous solution containing 0.2% (w/w) polyvinylpyrrolidone and 0.25 mM sodium dodecyl sulfate under sonication. The sonication was continued for 80 minutes. The resulting particles were crystalline with a mean hydrodynamic diameter of 160 nm.

Comparative Example 3

Example 3 was repeated except sonication was discontinued directly after mixing the two solutions. Stable amorphous particles were obtained with a mean hydrodynamic diameter of 90 nm. No crystalline material was observed.

Example 4

Bicalutamide

A solution of 100 mM bicalutamide in dimethyl sulfoxide was prepared. 0.020 ml of this solution was added rapidly to 1.980 ml of an aqueous solution containing 0.01% w/w polyvinylpyrrolidone (PVP) and 0.25 mM sodium dodecyl sulfate under sonication. The sonication was continued for 45 minutes. After sonication, 475 µl of a solution containing 1% w/w PVP was added to raise the concentration of PVP to 0.2% w/w. The resulting particles were crystalline with a mean hydrodynamic diameter of 190 nm and the particle size remained constant for at least 1 hour.

Comparative Example 4

Example 4 was repeated except sonication was discontinued directly after mixing the two solutions. The concentration of PVP was then raised to 0.2% w/w directly after the sonication, amorphous nano-particles were obtained with a mean hydrodynamic diameter of approximately 190 nm. The particle size was observed to increase over a period of 1 hour from 190 to 300 nm (probably as a result of Ostwald ripening).

Example 5

5-(4-chlorophenyl)-1-(2,4-dichlorophenyl)-4-methyl-N-piperidin-1-yl-1H-pyrazole-3-carboxamide A 100 mM solution of 5-(4-chlorophenyl)-1-(2,4-dichlorophenyl)-4-methyl-N-piperidin-1-yl-1H-pyrazole-3-carboxamide (described in EP 656 354) in dimethylacetamide was prepared. 0.010 ml of this solution was added rapidly to 0.990 ml of an aqueous solution containing 0.2% (w/w) polyvinylpyrrolidone (PVP) and 0.25 mM sodium dodecyl sulfate (SDS) under sonication. The sonication was continued for 75 minutes. The resulting particles were crystalline with a mean hydrodynamic diameter of 275 nm. The particle size remained constant for at least 2.5 hours.

Comparative Example 5

Example 5 was repeated except sonication was discontinued directly after mixing the two solutions. Amorphous nano-particles were obtained with a mean hydrodynamic diameter of approximately 220 nm. The particle size was observed to increase (probably due to Ostwald ripening) over a period of 2.5 hours from 220 to 340 nm.

Example 6

5-(4-bromophenyl)-1-(2,4-dichlorophenyl)-4-ethyl-N-piperidin-1-yl-1H-pyrazole-3-carboxamide A 100 mM solution of 5-(4-bromophenyl)-1-(2,4-dichlorophenyl)-4-ethyl-N-piperidin-1-yl-1H-pyrazole-3-carboxamide (described in WO00/46209) in dimethylacetamide was prepared. 0.010 ml of this solution was added rapidly to 0.990 ml of an aqueous solution containing 0.2% (w/w) polyvinylpyrrolidone and 0.25 mM sodium dodecyl sulfate under sonication. The sonication was continued for 35 minutes. The resulting particles were crystalline with a mean hydrodynamic diameter of 190 nm. The particle size remained constant for at least 1.5 hours.

Comparative Example 6

In another experiment where sonication was discontinued directly after mixing the two solutions, amorphous nanoparticles were obtained with a mean hydrodynamic of approximately 280 nm. The particle size increased due to Ostwald ripening over a period of 1.5 hours from 280 to 480 nm.

Example 7

5,6-bis(4-chlorophenyl)-N-piperidin-1-ylpyrazine-2-carboxamide

A 100 mM solution of 5,6-bis(4-chlorophenyl)-N-piperidin-1-ylpyrazine-2-carboxamide in dimethylacetamide (described in PCT GB02/05736) was prepared 0.010 ml of this solution was added rapidly to 0.990 ml of an aqueous solution containing 0.2% (w/w) polyvinylpyrrolidone and 0.25 mM sodium dodecyl sulfate under sonication. The sonication was continued for 60 minutes. The resulting particles were crystalline with a mean hydrodynamic diameter of 170 nm. The crystalline nano-particle size remained constant for at least 1.5 hours.

Comparative Example 7

Example 7 was repeated except sonication was discontinued directly after mixing the two solutions. Amorphous nanoparticles were obtained with a mean hydrodynamic diameter of approximately 210 nm. The particle size increased (probably as a result of Ostwald ripening) over a period of 1.5 hours from 210 to 260 nm.

The invention claimed is:

1. A process for the preparation of a dispersion of nanocrystalline particles in an aqueous medium, the process comprising the steps:
   (a) combining in less than 30 seconds a first solution and an aqueous phase under rapid mixing to form a dispersion of amorphous particles, wherein:
      (i) the first solution comprises a substantially water-insoluble substance in a water-miscible organic solvent, and
      (ii) the aqueous phase comprises water and optionally a stabilizer,
   (b) sonicating the dispersion of amorphous particles for at least 10 minutes to form nanocrystalline particles having a mean particle size of from 10 to 200 nm of the substantially water-insoluble substance; and
   (c) optionally removing the water-miscible organic solvent.

2. The process according to claim 1, wherein the substantially water-insoluble substance is a pharmacologically active compound.

3. The process according to claim 1, wherein the concentration of the substantially water-insoluble substance in the aqueous medium following step (a) is 10 mM or less.

4. The process according to claim 3, wherein the concentration of the substantially water-insoluble substance in the combined solution and aqueous phase following step (a) is from 0.5 to 3 mM.

5. The process according to claim 1, wherein the aqueous phase contains a stabiliser.

6. The process according to claim 5, wherein the stabiliser comprises a polymeric dispersant and an amphiphilic surfactant.

7. The process according to claim 6, wherein the amphiphilic surfactant is an anionic, cationic, or non-ionic surfactant.

8. The process according to claim 7, wherein the polymeric dispersant is polyvinylpyrrolidone and the anionic surfactant is sodium dodecyl sulfate.

9. The process according to claim 6, wherein the amphiphilic surfactant is at a concentration below the critical association concentration for the amphiphilic surfactant and polymeric dispersant.

10. The process according to claim 1, wherein rapid mixing comprises using sonication during the combination.

11. The process according to claim 1, wherein the first solution is added to the aqueous phase.

12. The process according to claim 1, wherein the dispersion of amorphous particles is sonicated at a temperature below 50° C.

13. The process according to claim 1, further comprising isolating the nano-crystalline particles after formation of the nanocrystalline particles or after removal of the water-miscible organic solvent.

14. The process according to claim 1, wherein the dispersion of amorphous particles is sonicated for 20 to 100 minutes.

15. The process according to claim 1. wherein the first solution is added to the aqueous phase, wherein the aqueous phase comprises water. a polymeric dispersant, and an amphiphilic surfactant, and the concentration of the substantially water-insoluble substance in the combined first solution and aqueous phase following step (a) is 10mM or less.

16. The process according to claim 15, wherein the first solution and aqueous phase are combined by rapid mixing using sonication during the combination.

* * * * *

UNITED STATES PATENT AND TRADEMARK OFFICE
CERTIFICATE OF CORRECTION

PATENT NO. : 7,780,989 B2
APPLICATION NO. : 10/521617
DATED : August 24, 2010
INVENTOR(S) : Skantze et al.

It is certified that error appears in the above-identified patent and that said Letters Patent is hereby corrected as shown below:

Title Page: References Cited at INID Code (56), add the following U.S. Patent Documents:

| | | |
|---|---|---|
| US-4,348,385 | 9/1982 | Synek |
| US-4,610,868 | 9/1986 | Fountain et al. |
| US-5,468,604 | 11/1995 | Zengerle et al. |
| US-5,665,331 | 9/1997 | Bagchi et al. |
| US-5,858,410 | 1/1999 | Muller et al. |
| US-2006/0134146-A1 | 6/2006 | Lindfors |
| US-2006/0141043-A1 | 6/2006 | Lindfors |
| US-2006/0198893-A1 | 9/2006 | Lindfors |
| US-2005/0009908-A1 | 1/2005 | Hedberg et al. |

Signed and Sealed this

Thirtieth Day of November, 2010

David J. Kappos
*Director of the United States Patent and Trademark Office*